Figure 1:
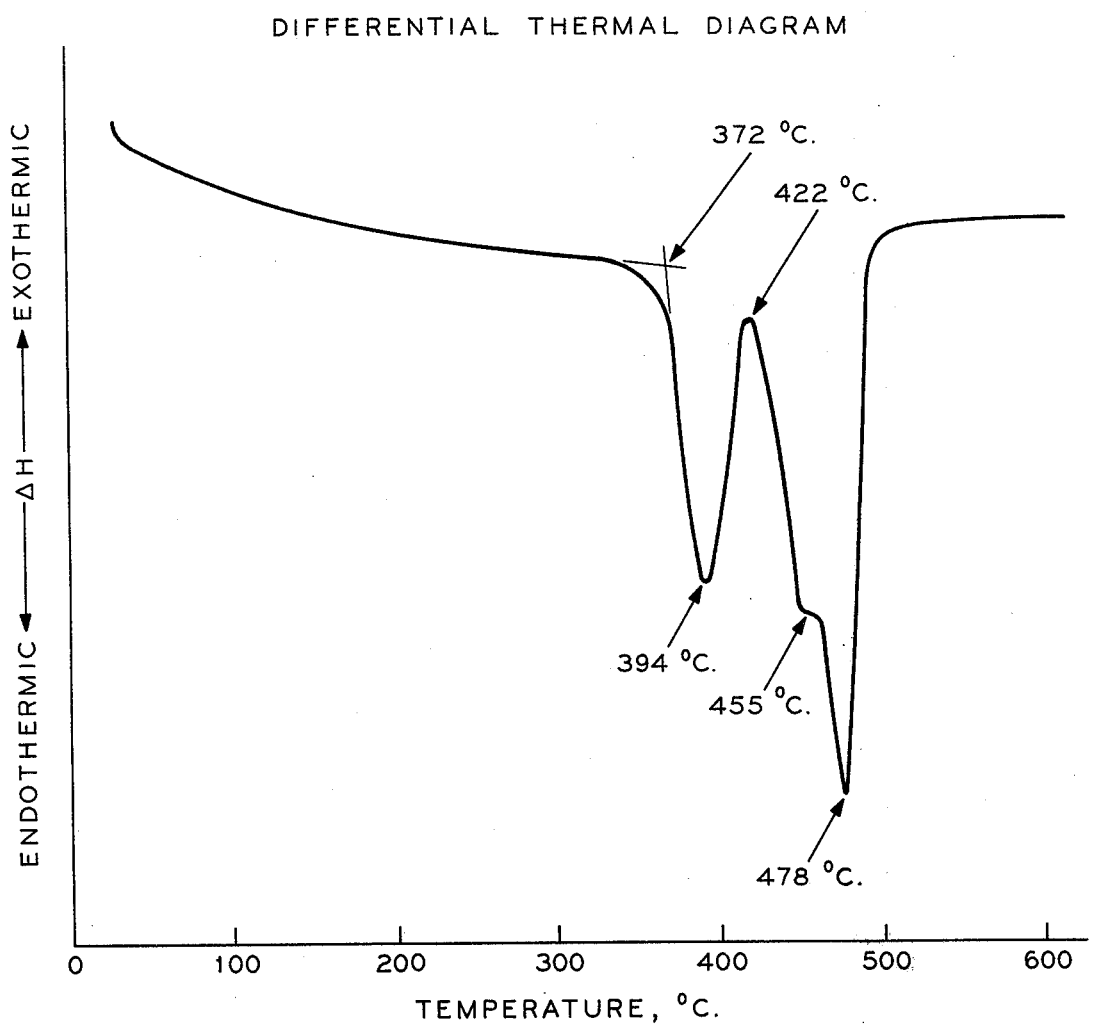

United States Patent [19]
Harrison

[11] 3,985,775
[45] Oct. 12, 1976

[54] VANADIUM-PHOSPHORUS OXIDE OXIDATION OF N-BUTANE TO MALEIC ANHYDRIDE

[75] Inventor: Jonas P. Harrison, Pinole, Calif.

[73] Assignee: Chevron Research Company, San Francisco, Calif.

[22] Filed: Mar. 18, 1974

[21] Appl. No.: 452,480

Related U.S. Application Data

[63] Continuation-in-part of Ser. No. 200,724, Nov. 22, 1971, abandoned.

[52] U.S. Cl. .................... 260/346.8 A; 252/435; 252/437
[51] Int. Cl.² ........................ C07D 307/60
[58] Field of Search .................... 260/346.8 A

[56] References Cited
UNITED STATES PATENTS

| | | | |
|---|---|---|---|
| 2,777,860 | 1/1957 | Egbert | 260/346.8 |
| 3,086,026 | 4/1963 | Wiebusch | 260/346.8 |
| 3,156,707 | 11/1964 | Kerr | 260/346.8 |
| 3,293,268 | 12/1966 | Bergman | 260/346.8 |
| 3,366,648 | 1/1968 | Kerr | 260/346.8 |

Primary Examiner—Natalie Trousof
Assistant Examiner—Barry Dentz
Attorney, Agent, or Firm—G. F. Magdeburger; John Stoner, Jr.; T. G. DeJonghe

[57] ABSTRACT

A high-activity vanadium-phosphorus mixed-oxide catalyst is prepared by a method requiring heating the catalyst precursor at about 350°–410°C. to drive off at least a portion of the water of hydration, and then at a higher temperature. The catalyst is especially useful for oxidation of n-butane to maleic anhydride.

2 Claims, 2 Drawing Figures

3,985,775

VANADIUM-PHOSPHORUS OXIDE OXIDATION OF N-BUTANE TO MALEIC ANHYDRIDE

RELATED APPLICATION

This application is a continuation-in-part of application Ser. No. 200,724, filed Nov. 22, 1971, now abandoned.

BACKGROUND OF THE INVENTION

This invention relates to a vanadium-phosphorus mixed-oxide oxidation catalyst which is particularly useful for maleic anhydride production.

The preparation of a mixed oxide comprising vanadium and phosphorus for use as a catalyst for a vapor-phase oxidation of a hydrocarbon feed is known in the art. In general, these oxidations suffer from a number of disadvantages, including relatively low yields of the desired product. For example, in the process of U.S. Pat. No. 3,293,268, a mixed-oxide catalyst of a vanadium-phosphorus composite is used to oxidize an n-butane feed to maleic anhydride. The oxidation temperatures employed are in the range 525°–600° C. and the yields are in the range 25–52 weight percent, based on the feed. The theoretical yield for the reaction $$n\text{-}C_4H_{10} + 7/2\ O_2 \rightarrow C_4H_2O_3 + 4H_2O$$

is 169 weight percent. The actual yield reported in the above patent reference is less than 33⅓% of theory.

SUMMARY OF THE INVENTION

In accordance with the present invention a process is provided for producing maleic anhydride from a hydrocarbon, which comprises contacting the hydrocarbon and an oxygen-containing gas with a catalyst comprising a mixed vanadium-phosphorus oxide under conditions sufficient to convert the hydrocarbon to maleic anhydride and wherein the catalyst is prepared by a. mixing and heating a vanadium compound with a phosphorus compound in the presence of a liquid medium to obtain a slurry containing a vanadium-phosphorus oxide hydrate,
b. removing liquid medium from the slurry to obtain the oxide hydrate,
c. heating the oxide hydrate in the presence of an oxygen-containing gas for at least 0.5 hour and at a temperature between about 350° and 410° C., preferably between about 360° and 400° C., to remove at least a portion of the water of hydration from the oxide hydrate and obtain a resulting oxide, and
d. heating the resulting oxide at a temperature above 410° C. and in the presence of an oxygen-containing gas.

Removal of liquid medium from the slurry as per step (b) can be by filtration and/or evaporative drying obtained by heating at a temperature below 340° C.

Typically the step (d) heating is carried out at a temperature at least 50° C. above the temperature used in step (c), preferably 75° to 120° C. above the temperature used in step (c), e.g., 450° to 520° C. Heating the oxide hydrate as per step (d) in an oxygen-containing gas preferably is done in a flowing gas, i.e., a gas stream, which gas stream preferably has a reduced oxygen content compared to air. Thus, for example, the step (d) heating can be carried out in an air-butane stream or an air-$H_2O$ stream, or in other streams of reduced oxygen content, for instance a gaseous stream containing about 2–19%, more preferably 5–15%, oxygen and the balance inerts such as nitrogen and $H_2O$ and/or $CO_2$, etc. It will be apparent from the description of the present invention that certain features of the invention may be altered while staying within the basic spirit of the invention. Thus, longer times at a slightly reduced temperature may result in somewhat comparable effects to a shorter length of time at a higher temperature. The present invention, in any case, requires heating a vanadium-phosphorus oxide hydrate at a first lower temperature plateau in the presence of a gas containing oxygen to drive off water of hydration, and then heating the resulting catalyst precursor material at a higher temperature, again in the presence of an oxygen-containing gas.

Among other factors, the present invention is based on my unexpected finding that using at least two high-temperature heating levels for the catalyst precursor with at least the first heating level being used to remove at least a portion of the water of hydration results in a generally more active catalyst than is obtained using one calcination temperature.

The mixed vanadium-phosphorus oxide hydrate, obtained after removing liquid as per step (b) above, is believed to have an empirical formula roughly as follows:

$$(V_2O_4)\cdot x(P_2O_5)\cdot y(H_2O)$$

wherein $x$ is in the range of about 0.9 to 2.0 and $y$ is in the range of about 1.7 to 2.5. As $y$ has been found to be about 1.7 to 2.5, at least in certain preparations using an aqueous medium, the catalyst precursor material of these certain aqueous preparations, before the 350°–410° C. heat treatment, can be referred to as an oxide "dihydrate", although the amount of water of hydration per mol of oxide complex generally is not exactly two mols. Similarly, if only about one mol of water is driven off at the 350°–410° C. heating plateau, the resulting material can be referred to as an oxide "monohydrate". In any case, in accordance with the present invention, water of hydration must be driven off for a period of at least about 0.1 hour, preferably at least 0.5 hour, at a temperature between about 350°–410° C., preferably 360°–410° C., before the catalyst is calcined at a higher temperature, for example 410°–540° C. Preferably the step (d) heating or calcination is carried out at a temperature between about 450° and 520° C.

Hydrocarbons which can be oxidized to maleic anhydride in accordance with the process of the present invention include benzene, butene and n-butane.

The catalyst of the present invention is especially advantageously used in the catalytic production of maleic anhydride from n-butane. Suitable reaction conditions include a reaction temperature from 350° to 500° C., more preferably 360° to 475° C., and a pressure of 5 to 100 psig, more preferably 10 to 50 psig. The oxidizing gas can be an oxygen-containing gas, such as air. Preferred amounts of n-butane in the air-hydrocarbon feed to the catalytic reactor are 1 to 10, more preferably 1 to 2, volume percent n-butane, but with due consideration given to the known explosion limits for butane-air mixtures. A butane ratio of 1.5 volume percent is most preferred. Preferably the particulate catalyst is disposed in a fixed bed. Preferred contact times for the butane-air feed are 0.1 to 10 seconds, preferably about 0.3 to 1.5 seconds.

The catalyst precursor material (oxide hydrate) which is to be heat-treated at 350°–410° C. can be prepared using an aqueous solvent or using a non-aqueous (organic) solvent or mixture thereof. The vanadium-phosphorus oxide hydrate preferably is prepared so that the valence of the vanadium is between about 4.0 and 4.5, and that of phosphorus is about 5.0, and the mols of water of hydration are between about 1.7 and 2.5. U.S. Pat. No. 3,293,268 describes generally suitable preparations for obtaining vanadium-phosphorus oxide dihydrates, using an aqueous solvent.

Thus, the oxide hydrate precursor of the catalyst of the present invention can be prepared by various methods, such as commonly known methods in which a vanadium compound and a pentavalent phosphorus compound are reacted in a liquid medium. The vanadium compound and the phosphorus compound can be dissolved in an aqueous medium. Preferably the vanadium compound and the phosphorus compound are reacted in a substantially non-aqueous medium. Non-aqueous solvents such as alcohols, ethers or carboxylic acids can be used, e.g., methanol, tetrahydrofuran, dimethoxyethane, and acetic acid. However, sufficient hydrogen ions and oxide or hydroxyl groups must be present so that the resulting catalyst precursor will be a hydrate, preferably approximately a "dihydrate", and preferably having about 1.5 to 2.5, more preferably about 2.0 to 2.3, mols of water of hydration per gram-atom of phosphorus. Any water which may be present in excess of the requirement for forming the desired hydrate is normally removed by maintaining the reaction mixture at a temperature below 350° C. Preferably the drying is carried out at or below 150° C. Under these conditions, drying can be effected in air without any substantial oxidation of the vanadium component by the oxygen in the air.

The oxide hydrate preparation is carried out in a liquid medium in which the reactants are brought into contact. The phosphorus component may be added, for example, as phosphorus pentoxide, phosphoric acid, phosphorus oxytrichloride, phosphoric acid esters, or a mixture of these reagents. The vanadium compound may be any one of a number of compounds, including vanadium pentoxide, vanadium tetroxide, vanadium oxalate, vanadium oxydichloride, vanadium oxydibromide, vanadium oxytrichloride, or mixtures and the like. Where dissolution of the reagents is desired, concentrated aqueous hydrochloric acid or hydrogen chloride gas may be added. In the presence of solubilizing acids, such as HCl, oxalic acid, etc., the reagents are mixed and heated until the solids are dissolved. At this point, the solution is usually red-brown in color. As this solution is concentrated, for example, by evaporation of water and volatile acids, such as hydrochloric, hydrobromic, and the like acids, the vanadium, if present in the +5 valence state, is reduced in the main to the +4 state, and the solution takes on the well-known blue coloration of vanadium (IV). However, in the absence of solubilizing agents, and in a nonaqueous medium, the vanadium component and the final mixed vanadium-phosphorus oxide product are essentially insoluble and remain as a slurry throughout the reaction. Heating is continued as before, until the slurry becomes blue.

If for some reason the necessary reduction does not occur, organic or inorganic reducing agents such as formaldehyde, acetaldehyde, or hydrogen, and the like (cf. U.S. Pat. No. 3,288,721) may be added as in a titration in amounts sufficient to produce the desired and characteristic blue solution. On the other hand, if by inadvertence, etc., over-reduction occurs (solution goes from red-brown to blue to black), then an oxidizing agent, such as hydrogen peroxide, may be added, again as in a titration, or the oxidation can be carried out by maintaining the pH of the solution below about 3 and passing air or oxygen into the solution until the blue or red-brown color develops. Where organic reagents or cosolvents are used in the preparation, the dihydrate may also contain an adsorbed or coordinate complex bonded organic component.

The relative amounts of the phosphorus and vanadium compounds satisfactory for use in the preparation of the mixed oxide dihydrate (catalyst precursor) is determined by the P:V atomic ratio desired. Excellent catalysts are obtained when this ratio is about 1.2. In general, useful catalysts are obtained by the method of the present invention when this ratio is in the range 0.9:1 to 2:1, preferably 1.0:1 to 1.5:1.

The present invention contemplates the catalyst prepared in accordance with the methods described herein as well as the catalyst preparation methods themselves and the use of the catalyst in production of maleic anhydride from a hydrocarbon, especially from n-butane.

DRAWINGS

Figure 2:
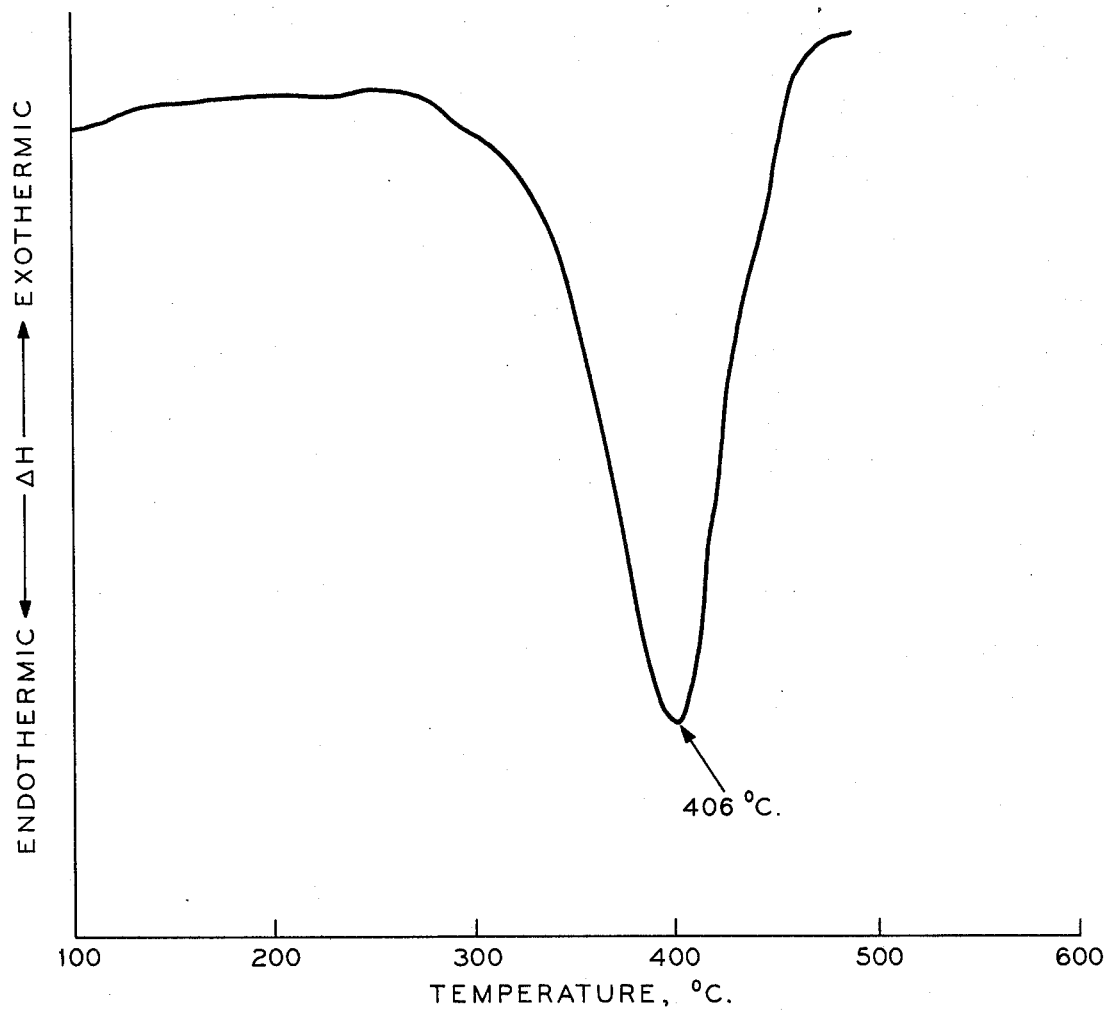

The drawings graphically represent the results obtained from differential thermal analyses (DTA) of complex vanadium (IV)-phosphorus (V) oxide hydrates. As shown in FIGS. 1 and 2, for catalyst preparations using aqueous as well as for catalyst preparations using a non-aqueous solvent, an endothermic dip was found in the DTA curves within the range of about 350°–410° C.

FIG. 2 illustrates the same effect as FIG. 1, occurring within the range of 350°–410° C., but without any further endotherms. Catalysts prepared in accordance with procedures as described in Example 15 have frequently been found to give DTA curves as in FIG. 2; also, catalysts prepared in accordance with examples such as Example 13 (aqueous preparation) have given on occasion DTA curves as in FIG. 2.

The first heating plateau that is best used within the range of about 350°–410° C. can be determined for a particular vanadium-phosphorus oxide hydrate catalyst material by running a DTA analysis for the particular material.

The DTA analytical technique is described in the art (see "Differential Thermal Analysis" by R. C. Mackenzie, Academia Press, London & New York, 1970, Chapter 11, pp. 343–361). These data demonstrate the bulk-phase transition temperatures discovered in the course of the research which ultimately led to the present invention. Briefly, the DTA method involves passing a steady flow of an inert gas, such as helium, through or above a bed of the solid material to be tested. The temperature difference between the solid and an inert reference is measured and compared. The temperature of the solid and reference is increased at a uniform, moderate rate, for example 10° C. per minute. Solid crystal-phase transitions are, in general, accompanied by an energy effect which is characteristic for the given change. In FIG. 1, for example, at about 372° C. (break in the curve of FIG. 1) and in the range 372°–394° C., a phase transition (likely the dihydrate to monohydrate) is demonstrated. Thereafter the oxide increases in temperature until at about 415°–425° C. another phase transition (monohydrate to substantially anhydride) starts to take place and appears to be completed at about 450° C. (short plateau in the curve), with a third transition (a crystal-phase change in the substantially anhydrous oxide) commencing at about 455° C. and being completed at a temperature of about 480° C.

EMBODIMENTS USING AN AQUEOUS PREPARATION

In a preferred aqueous-preparation embodiment, a vanadium (IV)-phosphorus (V) oxide dihydrate is prepared by dissolving vanadium pentoxide in concentrated aqueous hydrogen chloride and then adding 85% phosphoric acid to the resulting solution (see, for example, U.S. Pat. No. 3,293,268). The $V_2O_5$ and $H_3PO_4$ additions are made in amounts sufficient to yield a phosphorus to vanadium atomic ratio between about 0.5:1.0 and 2.0:1.0, preferably about 1.2:1.0. The resulting solution is then concentrated by heating until a thick aqueous slurry containing about 50% (weight) of solids is obtained. During this operation, much of the hydrogen chloride and water in the mixture is evolved. Also, the vanadium component is reduced from +5 to an average value of about +4. The thick slurry is then conveniently dried to constant weight in air by maintaining it at a temperature of about 150° C. During this drying, the loosely associated water is evolved, leaving a mixed-oxide residue which is substantially the dihydrate and in which the average valence of the vanadium component is about 4.2. It is a homogeneous, complex, mixed oxide.

For the processing of the dihydrate through the phase transitions, the dihydrate preferably is in particulate form. Depending upon the desired catalyst configuration, the dihydrate is either sized and screened or pulverized and mixed with sufficient liquid, e.g., water or alcohol, to form an extrudable paste. In the latter case, the paste is then extruded (for example using a 3/16 inch-diameter die), sized to a desired length (about ¼ inch) and dried in air at a temperature of about 150° C.

The dihydrate is then converted to the monohydrate by maintaining it at a temperature of about 385° C. in a stream of air (oxygen-containing carrier gas). Based upon the dihydrate charge, when the weight loss is about 5% the dihydratemonohydrate phase transition is completed.

Next the monohydrate is converted to the anhydrous oxide by raising its temperature to about 410° C. and passing a carrier gas mixture such as n-butane/air (1.5 volume percent n-butane) through the oxide. A contact time for the carrier gas of about 5 seconds is satisfactory. After an additional weight loss by the charge of about 5%, this stage is completed.

Finally, the substantially anhydrous oxide is heat treated in an oxygen-containing gas stream such as the above n-butane/air at a temperature of about 480° C. for about 5 hours. The resulting complex composite, after a relatively short runin period (16 to 30 hours) under vapor-phase hydrocarbon oxidizing conditions, exhibits an excellent activity, selectivity and catalyst life.

It is to be understood that the above description is a preferred embodiment. The exact procedure and amount of water of hydration may vary within the spirit of the present invention, but, in any case, the present invention requires heating a vanadium-phosphorus oxide hydrate at a first lower temperature plateau in the presence of a gas containing oxygen to drive off water of hydration, and then heating the resulting catalyst precursor material at a higher temperature, again in the presence of an oxygen-containing gas.

EMBODIMENT USING A NON-AQUEOUS PREPARATION

Catalyst hydrate precursors can also be prepared in non-aqueous media. For instance, a vanadium oxyhalide or $V_2O_5$ and a hydrohalide are dissolved in an organic medium, e.g., tetrahydrofuran, dimethoxyethane, acetic acid, etc., and heated with a phosphorus compound, e.g., phosphoric acid or a phosphorus oxyhalide. The resulting vanadium-phosphorus mixed oxide is isolated by evaporation of the solvent.

Thus, the liquid medium used to dissolve or suspend the vanadium and phosphorus compounds in the present invention can be either predominantly aqueous, e.g., entirely aqueous or 60% to 95% by weight aqueous with the balance organic liquid, or predominantly organic, or at least 60% to 80% by weight organic with the balance aqueous.

STANDARD CATALYST TEST

In order to compare oxidation catalysts in a meaningful manner herein, a test was required and developed. Two primary factors are involved: (a) activity, and (b) selectivity. The temperature at which the use of a given catalyst results in a 90% conversion of hydrocarbon feed at a 1-second contact time was found to be a good measure of the activity of the catalyst, and one which can be conveniently determined. The yield of the desired product (maleic anhydride) based on the feed converted (90% in the standard test) is the measure of the selectivity of the catalyst.

EXAMPLES

The following examples further illustrate the invention. The selectivities in the samples are percent yields based on the number of pounds of maleic anhydride produced per pound of n-butane converted. In these examples, all parts are by weight unless otherwise indicated.

EXAMPLES 1–12

In the examples of Table I, a representative vanadium-phosphorus mixed-oxide hydrate was prepared by mixing vanadium pentoxide with concentrated aqueous hydrochloric acid and heating the mixture until solution of the vanadium oxide was complete. Phosphoric acid (85 weight percent) was then added to the blue vanadium oxydichloride solution obtained from the acid treatment in a relative amount sufficient to yield an atomic ratio of phosphorus to vanadium of about 1.2. The aqueous vanadium oxydichloride-phosphoric acid solution was then concentrated by evaporating water at a temperature of about 100° C. until a thick slurry was produced. The wet slurry was then dried to constant weight by heating at a temperature of 150° C. in a ventilated oven. The dried mixed oxide, approximately a dihydrate, and for simplification referred to herein as a dihydrate, was then broken up by mechanical means and sized to the 20–28 mesh (U.S. Standard) range. It had a surface area (B.E.T. Method) of about 3 m²/g.

In the procedure described below, aliquots (10–20 cc) of the dried mixed-oxide dihydrate were placed in a ½ inch-diameter (No. 316SS or aluminum) reaction tube and given the indicated pretreatment. The resulting catalysts were then evaluated under the standard test conditions (90% conversion, 1-second contact time, etc.) in a vapor-phase oxidation reactor. The maleic anhydride content of the effluent gas stream from the reactor was condensed and determined by a routine caustic titration using phenolphthalein indicator (results were confirmed by polarographic and potentiometric titration methods). The n-butane/air feed stream was analyzed using gas-chromatographic methods supplemented by occasional fixed-gas analysis in a Fisher gas partitioner unit. The results of the tests and analyses are listed in Table I.

TABLE I

| | | CATALYST PERFORMANCE | | | |
|---|---|---|---|---|---|
| Ex. No. | Pretreatment Method | Standard* Activity, °C. | Selectivity** | Space Rate, V/V/Hr. | Run Time, Hrs. |
| 1 | A | 525 | >70 | 700 | 100–300 |
| 2 | B | 470 | 90 | 780 | 287 |
| 3 | C | 465 | 97 | 813 | 113 |
| 4 | D | 460 | 89 | 750 | 120 |
| 5 | E | 450 | 91 | 750 | 160 |
| 6 | F | >550 | — | 750 | 160 |
| 7 | G | >550 | — | 750 | 160 |
| 8 | H | 478 | 86 | 700 | 530 |
| 9 | I | 485*** | 84 | 672 | 285 |
| 10 | J | 492 | 78 | 810 | 162 |
| 11 | K | 535 | — | 750 | 49 |
| 12 | L | 520 | — | 750 | 49 |

*90% conversion, 1-second contact time & 1.5 volume percent n-butane in air
**Weight percent yield based on n-butane converted
***Activity increasing with time on stream

PRETREATMENT METHOD

A. Conventional pretreatment: Mixed oxide temperature increased from 250° to 500° C. at a rate of 200° C. rise per hour; an air-butane mixture containing 1.5 volume percent of n-butane contacted with the oxide at 700 V/V/hr.

B. 2-Stage transition phase pretreatment:
   1. mixed-oxide dihydrate heated from 250° C. to 385° C. in the presence of air at 1 atmosphere pressure flowing at the rate of 120 V/V/hr, thereafter maintaining the temperature at 385° C. for about 1 hour at 120 V/V/hr to obtain a monohydrate;
   2. heating the monohydrate to 414° C. and maintaining the temperature at 414° C. while passing an air/n-butane mixture (1.5 volume percent n-butane) through the oxide at 120 V/V/hr; and
   3. increasing the n-butane/air mixture flow rate to 700 V/V/hr while heating the oxide up to about 470° C. at a rate of temperature rise of about 5°–10° C. per hour.

C. As in B), except in step (1) the air pressure was 25 psig.

D. As in B), except the heating started with the mixed oxide at the ambient temperature initially and using 200 V/V/hr of air.

E. Stepwise heating at 300 V/V/hr in:
   1. air at 360° C.;
   2. 1.5% n-butane in air to 385° C. and hold for 1 hour;
   3. to 415° C. and hold for 1 hour;
   4. to 460° C. and hold for 1 hour (all temperature increases at the rate of 5°–10° C. per minute); and
   5. Use of catalyst at 500° C. (1.5% butane/air), reducing temperature until activity lined out at standard test conditions, i.e., 90% conversion, 1-second contact time, etc.

F. As in (E), step (1), except the temperature was raised to 420° C., followed by step (5) of (E).

G. As in (F), but there was no flow of air in step (1) after which step (5) of E was carried out.

H. The dried mixed-oxide dihydrate was heated from 260° C. at 1.8° C. per minute temperature rise to 480° C. while passing air/n-butane (1.5% n-butane) at 90 V/V/hr. The catalyst was then maintained at 480° C. for 65 hours while passing the n-butane/air through the catalyst at 90 V/V/hr, after which the feed rate was increased to 700 V/V/hr.

I. The mixed oxide was prepared as described above, and dried at about 150° C. The dried solid was then ball-milled and mixed with water to make a paste, which was then extruded as ⅛ inch-diameter rods and cut to convenient lengths. After drying again at about 150° C., the catalyst pellets were activated as in method (B) above.

J. As in (B), except step (1) with air/n-butane flow at 1500 V/V/hr at 25 psig, followed by steps (2) and (3).

K. The dried mixed-oxide dihydrate was heated up in hydrogen gas at 300 V/V/hr to 360° C, held at 360° C for 2 hours and then brought to the reaction temperature while passing 1.5% n-butane/air mixture at 700 V/V/hr over the catalyst.

L. The dried mixed-oxide dihydrate was heated in n-butane to 360° C. at 300 V/V/hr, maintained at 360° C for 2 hours, and then heated to reaction temperature at 700 V/V/hr in 1.5% n-butane/air.

EXAMPLE 13

A reactor was charged with 32.9 parts of 37% aqueous hydrochloric acid and 1.83 parts of vanadium pentoxide. The mixture was stirred and slowly heated to 35° C. After holding the reaction mixture at 35° C. for one-half hour, the temperature was increased to 79° C. at a rate of about 0.5° C. per minute. After 1.5 hours at 79° C., the temperature was increased to about 100° C. and the mixture was allowed to reflux for about 5 hours. The resulting solution was clear, and had a blue color.

The solution was cooled to about 65° C. and 2.77 parts of 85% aqueous phosphoric acid was added. Then the temperature was again raised to 100° C. At this temperature, water and hydrogen chloride were distilled off until the mixture had lost 60% of its volume. The reactor was cooled to 37° C. and the blue solution was poured into Pyrex trays.

The trays of blue solution were placed in a forced-air oven at 150° C. and were evaporated to dryness in about 16 to 24 hours. The resulting solid was ground to a particle size less than 20 mesh. This dry powder was blended with 15 weight percent water and was extruded through a ⅛ inch-diameter die. This extrudate was sized into particles, ⅛ to ¼ inch long, and then air dried for 16 hours at 150° C.

The particles were placed in a vertical 1.5 × 4 inches ceramic-lined reactor tube having a ⅛ inch thermowell. The reactor was heated to 385° C. and held at that temperature for 2 hours, all under an air flow of 120 to 200 volumes per hour per volume of catalyst at a pressure of 25 psig. For the first 6 batches, the water given off during the heat-treating period was collected in an ice trap, and at the same time the loss in weight of the charge was measured. The results were as follows:

| Batch | Solid Particles | | Recovered Water | |
|---|---|---|---|---|
| | Charged (grams) | Recovered (grams | (grams | (%) |
| 1 } 2 } | 1411 | 1033 | 115 | 10.0 |
| 3 | 577 | 517 | 66.1 | 11.5 |
| 4 | 390 | 350 | 43.3 | 11.1 |
| 5 | 391 | 355 | 41.1 | 10.5 |
| 6 | 387 | 347 | 34.8 | 10.0 |

Assuming the charge to this heat treatment to have a molecular formula of $(V_2O_4)(P_2O_5).nH_2O$, the above-described dehydrations give a value of n in the range 1.7 to 2.2; that is, the charge appears to be chiefly a dihydrate of a complex mixed vanadium-phosphorus oxide.

The particles, after cooling, were charged to a vertical catalytic vapor-phase oxidation reactor. The reactor was placed in a salt bath and was heated to 454° C. at a rate of 2° C. per minute while passing a 1.5% butane-in-air mixture over the catalyst particles at 120 to 200 space velocity. Heating in the presence of a butane-air mixture was continued at 454° C. for 16 hours. Essentially no water was evolved during this heating step.

After the above activation procedure, the catalyst was tested in a ¾ inch-diameter × 20 inch-long reactor wherein the butane-air rate and the temperature were adjusted to give maximum yield of maleic anhydride. After 800 hours of steady operation, the air-butane rate was adjusted to give a 1-second contact time (578 $hr^{-1}$), and the temperature was adjusted to give a 90% conversion of butane (453° C.). Under these conditions, the selectivity was 81 weight percent. After cooling, the catalyst was removed from the reactor. It had a surface area of 3.2 $m^2/g$ and a vanadium valence state of +4.1.

EXAMPLE 14

A reactor was charged with 3.78 parts of vanadium pentoxide and 22.3 parts of tetrahydrofuran (THF). The mixture was stirred vigorously. Then 1.35 parts of water was added. Next, 7.67 parts of phosphorus oxychloride was added slowly, so that the THF refluxed gently. After 16 hours of stirring at room temperature, a green solution was obtained.

The THF was removed by distillation, to leave a brown, friable solid which was dried in a forced-air oven at 150° C. The dried product was broken up and sieved through a 20-mesh screen. It was then formed into ⅛ inch-diameter × ¼ inch-long extrudates, as described in Example 13, using 20% isobutyl alcohol in place of water.

The dried extrudate was activated in a ¾ inch-diameter × 10 inches-long reactor utilizing the same procedure as in Example 13, except that the heat-treating step with a 1.5% butane-in-air mixture followed immediately after the 2-hour, 385° C. treatment, without interstep cooling.

This catalyst was then utilized to promote air oxidation of butane to maleic anhydride in the same apparatus as in Example 13. After 160 hours on stream, the air-butane rate was adjusted to 578 $hr^{-1}$ (1-second contact time) and the temperature was then adjusted to give a butane conversion of 90% (418° C.). The resulting selectivity was 114 weight percent.

After removal from the reactor, this catalyst had a surface area of 23.1 $m^2/g$ and a vanadium oxidation state of +4.1.

EXAMPLE 15

A catalyst precursor was prepared in an organic solvent using 10.2 parts of vanadium pentoxide and 14.35 parts of 100% phosphoric acid. The solid catalyst precursor was removed from the organic solvent (reaction liquid) by filtration. The wet cake weighed 32.25 parts and was air dried for 2 hours. Final drying was in an oven at 158° C. for 2 hours. In this way, there was obtained 20 parts of a vanadium-phosphorus mixed-oxide hydrate.

A sample of the above material was subjected to a thermogravimetric analysis wherein the atmosphere was helium and the heating rate was 10° C. per minute. No further weight loss occurred beyond 625° C. The total loss in weight was 21%, of which 7.5% was water. This corresponds to an initial 1.4 mols of water per mol of the vanadium-phosphorus oxide (calculated as before). This water is referred to herein under the general heading of "water of hydration," as the water is associated with a solid that has been dried at a temperature above room temperature, typically between about 25° and 200° C.

A portion of the mixed oxides was dampened and extruded to form ⅛ inch-diameter by ¼-inch to ⅜ inch-long extrudates. It was then activated by the process of this invention and was found to be a very satisfactory catalyst for the air oxidation of n-butane to maleic anhydride.

EXAMPLE 16

Another vanadium-phosphorus mixed oxide catalyst precursor was prepared by essentially the same procedure as was used in Example 15. After the final oven drying, a portion of the catalyst was analyzed. The vanadium-to-phosphorus ratio was 1.03:1 and the surface area was about 20 $m^2/g$. A differential thermal analysis gave the endotherm shown in FIG. 2. This later analysis was run at a temperature rise of 10° C. per minute in nitrogen gas flowing at 30 ml per minute.

Another portion of the precursor was extruded into ⅛ inch-diameter pellets. These pellets were charged to a vertical, fixed bed reactor 12½ inch long by ¾ inch internal diameter. A ¼ inch thermowell passed through the center of the bed. The pellets were then activated by first heating at 380° C. in the presence of air for 2 hours. Then the temperature was raised to 480° C. over a period of 1 hour, during which time a 1.5% butane-in-air mixture was passed over the pellets. Heating was continued at 480° C. for about 16 hours.

After this activation, the catalyst was used to catalyze the air oxidation of n-butane to produce maleic anhydride. After 547 hours on stream, the temperature required to give a 90% conversion of butane at a 1-second contact time was 435° C. The selectivity was 100 weight percent.

What is claimed is:

1. A process for producing maleic anhydride from n-butane which process comprises contacting the n-butane and an oxygen-containing gas with a catalyst comprising a mixed vanadium-phosphorus oxide under conditions sufficient to convert the n-butane to maleic anhydride and wherein the catalyst is prepared by
   a. mixing and heating a vanadium compound with a phosphorus compound in the presence of a liquid medium to obtain a slurry containing vanadium-phosphorus oxide hydrate,
   b. removing liquid medium from the slurry to obtain vanadium-phosphorus oxide dihydrate,
   c. heating the oxide dihydrate, at a temperature which is maintained between 350° and 410° C., in the presence of an oxygen-containing gas for a period of time sufficient so as to remove about one mol of the water of hydration from the oxide dihydrate and obtain a resulting monohydrate oxide, and thereafter
   d. heating the resulting monohydrate oxide at a temperature above 410° C. in the presence of an oxygen-containing gas.

2. A process in accordance with claim 1 wherein the contacting of the n-butane and the oxygen-containing gas with the catalyst is carried out under maleic anhydride production conditions which include a temperature between about 350° and 500° C.

* * * * *